United States Patent [19]
Burogyne, Jr. et al.

[11] Patent Number: 5,072,046
[45] Date of Patent: Dec. 10, 1991

[54] BIS-(AMINOPHENYL KETONES) COMPOUNDS

[75] Inventors: William F. Burogyne, Jr., Emmaus; Mark D. Conner, New Tripoli; Michael E. Ford, Coopersburg; Thomas A. Johnson, Orefield, all of Pa.

[73] Assignee: Air Products and Chemicals, Inc., Allentown, Pa.

[21] Appl. No.: 416,291

[22] Filed: Oct. 2, 1989

[51] Int. Cl.$^5$ ................ C07C 225/22; C07D 339/04; C07D 307/02
[52] U.S. Cl. ...................... 564/328; 549/13; 549/22; 549/74; 549/357; 549/496
[58] Field of Search .......................... 564/328

[56] References Cited

U.S. PATENT DOCUMENTS

| | | | |
|---|---|---|---|
| 3,063,966 | 11/1962 | Kwolek et al. | 260/78 |
| 4,101,487 | 7/1978 | Peterson | 260/29.2 N |
| 4,339,568 | 7/1982 | Maresca | 528/126 |
| 4,393,162 | 7/1983 | Paschke et al. | 524/606 |
| 4,657,990 | 5/1987 | Daoust et al. | 525/471 |
| 4,663,484 | 5/1987 | Horstmann | 564/430 |
| 4,687,833 | 8/1987 | Clendinning et al. | 528/125 |

FOREIGN PATENT DOCUMENTS

275035A2 7/1988 European Pat. Off.

OTHER PUBLICATIONS

Milto et al. Chem. Abstr. Acts; vol. 111, No. 23; 214163q (1989).
Schoenberg et al., Chem. Abstracts; vol. 99, No. 10; 71346x (1983).
Hergenrother, P. M., Wakelyn, N. T., and Havens, S. J. "Polyamides Containing Carbonyl and Ether Connecting Groups" Journal of Polymer Science: Part A Polymer Chemistry, vol. 25, 1093–1103 (1987).

*Primary Examiner*—Johann Richter
*Attorney, Agent, or Firm*—Russell L. Brewer; James C. Simmons; William F. Marsh

[57] ABSTRACT

This invention relates to a process for producing bis-[aminophenyl ketones] and the resulting compositions which are suitable for the preparation of engineering polymers, e.g., polyimides, polyurethanes and a host of other resinous materials. The bis-[aminophenyl ketones] are formed by reacting 2 moles of a nitrophenyl acid halide with an aromatic bridging composition having at least two hydrogen atoms of sufficient reactivity to undergo acylation reactions whereby nitrophenyl ketone groups are attached to the aromatic bridging group. The resulting bis-[nitrophenyl ketones] then are converted to the amine by hydrogenation or by double nucleophilic displacement with an aminophenol.

The invention also relates to polyimides and polyamides prepared from such bis-[aminophenyl ketones].

14 Claims, No Drawings

5,072,046

BIS-(AMINOPHENYL KETONES) COMPOUNDS

TECHNICAL FIELD

This invention relates to a process for forming bis-[aminophenyl ketones] which are suited for the preparation of engineering polymers such as polyamides and polyimides or polyurethanes.

BACKGROUND OF THE INVENTION

Wholly aromatic polyimides are well known and are prepared by reacting an aromatic diamine with an aromatic tetracarboxylic acid dianhydride under conditions which result in initial formation of a polyamic acid. On further reaction, the polyamic acid cyclizes to form the polyimide. Polyimides are well known for their outstanding engineering properties and, in particular, their thermal, oxidative and chemical resistance. Polyamides are formed by reacting a diamine with an aromatic dicarboxylic acid dichloride or diester, as opposed to the aromatic tetracarboxylic acid dianhydride, which then reacts to form the polyamide. Polyamides, like polyimides, have good thermal stability and excellent strength. Processing is often difficult because of their limited solubility in many organic materials.

Recently, Hergenrother, et al. at Langley Research Center, had an article published in the Journal of Polymer Science: Part A: Polymer Chemistry, vol. 25, 1093-1103 (1987) pertaining to new developments in polyimides. Specifically, polyimides containing both carbonyl and ether connecting groups were reported. These new polyimides were considered to be highly processable, and had excellent solvent and impact resistance. In the preparation of these polyimides containing carbonyl and ether connecting groups, the diamine monomers, particularly 1,3-bis[4-(4-aminophenoxy)benzoyl]benzene, were synthesized by aromatic nucleophilic displacement of fluorine from an activated substrate, e.g., the above-mentioned diamine was made by reaction of 1,3-bis[4-fluorobenzoyl]benzene with 4-aminophenol in the presence of potassium carbonate. More particularly, the process route is shown by the following formulas:

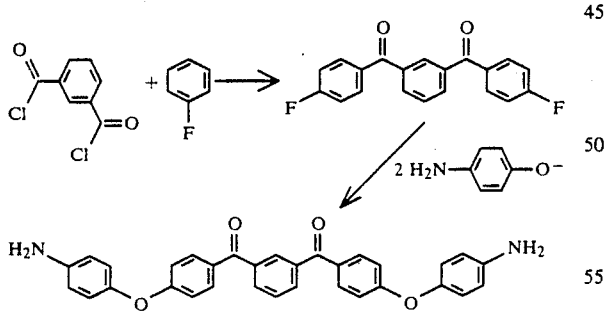

U.S. Pat. No. 4,393,162 discloses the preparation of polyimides and copolyamides prepared from di(aminophenoxy)ethane as the diamine monomer. The diamine monomer is then reacted with aromatic or aliphatic diacids.

U.S. Pat. Nos. 4,687,833; 4,339,568; and 4,657,990 and European Patent 275,035 disclose various aromatic and chain extended polyketones which were alleged to have excellent toughness, fabricability, high temperature and solvent resistance. In the '833 patent, a diphenol was coupled with a monomeric poly(arylether ketone) segment via a nucleophilic route using a base and aprotic solvent. The route was similar to that of Hergenrother, et al. for preparing the diamine monomer for preparing polyimides, except for the substitution of a diphenol for an aminophenol.

U.S. Pat. No. 4,663,484 discloses a process for producing diaminoalkyl diphenyl ethers by reacting alkylphenols with alkylhalobenzenes in the presence of a copper catalyst. These alkyldiphenyl ethers then were reacted with hydroxylamine to form the corresponding dioximes and then were subjected to a Beckman rearrangement followed by hydrolysis of the resulting diacetamino-alkyldiphenyl ether.

U.S. Pat. Nos. 3,063,966 and 4,101,487 discloses a process for producing aromatic polyamides by reacting an aromatic diamine with an aromatic diacid halide.

SUMMARY OF THE INVENTION

This invention pertains to a process for producing bis-[aminophenyl ketones] which are well suited for producing both polyamides, polyimides, polyurethanes and other elastomers and resins. The bis-[aminophenyl ketones] are formed from bis-[nitrophenyl ketones] by catalytically hydrogenating the nitro group to amine groups or by double nucleophilic displacement with an aminophenyl. The bis-[nitrophenyl ketones] are formed by reacting a composition of the formula:

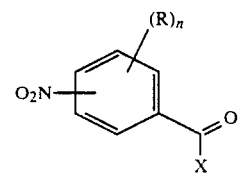

wherein R is hydrogen, or $C_{1-4}$ alkyl, n is 0 to 2 if R is $C_{1-4}$ alkyl and X is chlorine or bromine;
with an aromatic bridging composition of the formula

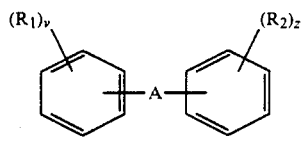

wherein $R_1$ and $R_2$ are hydrogen, or $C_{1-4}$ alkyl, v and z are 0-2 if $R_1$ and $R_2$ are alkyl;
A is represented by

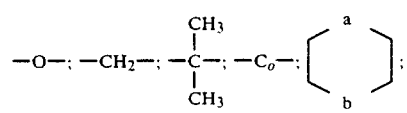

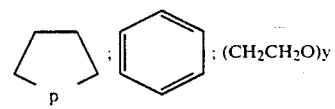

where y is 2 to 10; m/p phenylene;
wherein p is $-CH_2-$, O, or S,; and b is O or S a is $-CH_2-$, O, or S and b is O or S and a and b need not be identical. The resulting bis-[nitrophenyl ketones] are represented by the formula

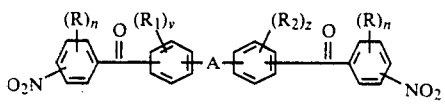

where R, $R_1$, $R_2$, n, v, z and A have the values listed above.

The bis-[aminophenyl ketones] produced by catalytic hydrogen of the bis-[nitrophenyl ketones] are represented by the formula wherein $R_1$, $R_2$, n, v, z and A have the values above.

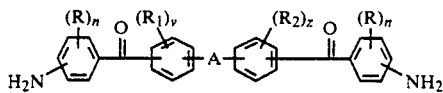

The bis-[aminophenyl ketones] produced by double nucleophilic displacement with an amine phenol are represented by the formula wherein $R_1$, $R_2$, n, v, z and A have the values above and Ar is phenylene or naphthalene.

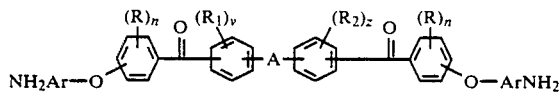

There are several advantages associated with the bis-[aminophenyl ketones] as described herein. These are:

an ability to produce bis-[aminophenyl ketones] where the amino groups may be in either the para or meta position. In the past, the amine groups in an aminophenyl ketone-type polyimide or polyamide were essentially limited to the para-position;

an ability to utilize bridging groups in the present compositions which may be varied;

an ability to produce a variety of polyamides and polyimides which can exhibit excellent modulus, tensile, thermal stability, solubility in dimethylacetamide and the like; and an ability to achieve a variety of unique properties in polyimides and polyamides heretofore unobtainable.

DETAILED DESCRIPTION OF THE INVENTION

Bis-[nitrophenyl ketones] are precursors to the bis-[aminophenyl ketones] suitable as aromatic diamine reactants for the formation of polyamides and polyimides having ketone linkages. The bis-[nitrophenyl ketones] are prepared in accordance with the process of this invention by reacting 2 moles of a nitrophenyl acid halide of the formula as described above with 1 mole of an aromatic bridging composition having at least two active hydrogens represented by the formula as described above.

Representative nitrophenyl acid halide compositions used for the reaction with the aromatic bridging composition are:

4-nitrobenzoyl chloride; 3-nitrobenzoyl chloride; 4-nitrobenzoyl bromide; 3-nitrobenzoyl bromide; 2-methyl-4-nitrobenzoyl chloride; 3-methyl-4-nitrobenzoyl chloride; 2-nitrobenzoyl chloride; and 2-nitrobenzoyl bromide.

A variety of aromatic and substituted aromatic bridging compositions may be used so long as there are two active hydrogens capble of acylation with the nitrobenzoyl halide coreactant. The aromatic bridging compositions, therefore, embrace a wide variety of structural components and thereby permit wide latitude in forming the structure of the precursor bis-[nitrophenyl ketones] for bis-[aminophenyl ketones]. The aromatic bridging composition permits modification of numerous physical properties in a polyimide or polyamide polymer system derived from the diamine monomer, e.g., thermal stability, processability, solubility, as well as solvent resistance, strength, resilience and other mechanical properties. The Hergenrother, et al. type diamine monomers, e.g., 1,3-bis-[4-(4-aminophenoxy)-benzoyl]benzene were limited because the bridging group was limited by the aromatic diacid halides that could be used in the Friedel-Crafts acylation of fluorobenzene. Structurally, and, in contrast to the Hergenrother et al. type diamines, the nitrobenzoyl halides become a terminal portion of the initial molecule rather than the bridging portion as in the Hergenrother, et al. molecule. Hence, even though both the present and Hergenrother, et al. diamine monomers contain ketone, and if desired ketone and ether linkages, properties of the resultant polymers are different because of the different structural relationship between the diamine molecules.

The aromatic bridging compositions typically are polynuclear aromatic compositions which may be fused or bridged with various alkylene, alkylene oxide or ether linkages. Representative aromatic bridging compositions are represented by the structure:

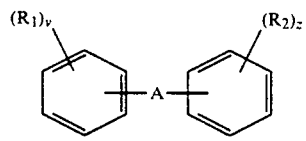

where A, $R_1$, $R_2$, v, z, are as shown above. Specific examples include diphenylether, dibenzodioxine, meta-terphenyl, para-terphenyl, fluorene, anthracene, biphenyl, dibenzofuran, alkyldiphenylethers where the alkyl group may have from 1 to 4 carbon atoms, e.g., 2-methyl-diphenylether, 3,3'-dimethyl diphenylether, 1,2-diphenoxyethane, bis(2-phenoxyethyl)ether, and the like.

The process for preparing the bis-[nitrophenyl ketones] utilizes a nitrobenzyl halide and an aromatic bridging composition having two active hydrogen atoms capable of undergoing acylation with the nitrobenzyl halide. The molar basis for the reaction is 2 moles nitroenzoyl halide per mole of aromatic bridging composition. Hydrogen halide is liberated as by-product. Although the stoichiometry is 2 moles nitrobenzoyl halide to 1 mole aromatic bridging composition, it will be recognized that in conducting the reaction other mole ratios may be used depending on the reactivity, etc. The acylation reaction typically is carried out at temperatures ranging from about 20° to 125° C. and pressures ranging from about 14.7 to 200 psig. The reaction may be carried out in liquid phase utilizing an inert organic solvent. Examples of inert organic solvents include methylene chloride, 1,2-dichloroethylene, and so forth.

Once the bis-[nitrophenyl ketone] is formed, the nitro groups may be converted to amine groups by catalytic reduction in the presence of a hydrogenation catalyst. Mild hydrogenation should be utilized so that the nitro groups are reduced without substantial ring or ketone hydrogenation. Examples of hydrogenation catalysts suited for effecting reduction of the nitro group to the amine include Raney nickel, rhodium, cobalt and other Group VIII and Group VI metals, especially platinum. Hydrogenation pressures ranging from 15 to 750 psig at hydrogenation temperatures of about 25° to 125° C. may be used for this reduction. Because the nitro groups any be in the meta or para position, differential properties in the polymer can be introduced into the molecule. For example, para-diamines lead to polymers with higher Tg, tensile strength and flex modulus.

An alternate method of producing the bis-[aminophenyl ketones] is by nucleophilic displacement of the nitro groups with aminophenoxy compositions, e.g., meta or para aminophenol or 4-aminonapthol in the presence of base. In contrast to the reduction process where the nitro groups are converted to the amine by catalytic hydrogenation, the nucleophilic displacement route using two moles of aminophenol introduces aromatic ether groups into the backbone of the polymer. The resulting structure of the molecules more nearly approximates those molecules of Hergenrother, et al. in which the fluorine groups undergo nucleophilic displacement with an aminophenol in the presence of base.

Representative bis-[aminophenyl ketones] produced by the mild catalytic hydrogenation of the bis-[nitrophenyl ketones] then are as follows:

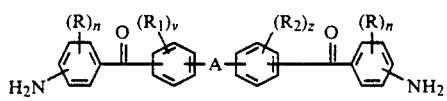

Representative bis-[aminophenoxyphenyl ketones] produced by nucleophilic displacement are represented by the formula:

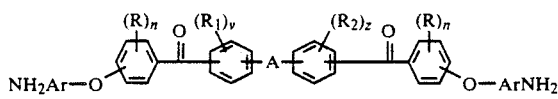

wherein Ar = phenylene or naphthylene

Polyimides and polyamides are formed from the resulting bis-[aminophenyl ketones] by reacting such diamines with an aromatic tetracarboxylic dianhydride or reacting the diamine with an aromatic dicarboxylic diacid halide. Examples of aromatic carboxylic acid anhydrides suited for polyimides are benzophenonedicarboxylic acid anhydride; and phthaloyl chlorides such as isophthaloyl chloride. U.S. Pat. No. 3,063,966 and U.S. Pat. No. 4,101,487 disclose numerous conventional methods for producing polyimides and polyamides and such reactants and processes are incorporated by reference.

The following examples are provided to illustrate various embodiments of the invention and are not intended to restrict the scope thereof.

EXAMPLES 1-6

Preparation of bis 4-[nitrobenzoyl]arenes

A Series of bis -[nitrobenzoyl]arenes was produced using the following general procedure. Anhydrous aluminum trichloride (24.57 gm, 0.184 mole) and dichloroethane (175 ml) were added to a 500 ml three-neck round bottom flask. The flask was equipped with a magnetic stir bar, condenser, static nitrogen line and a thermowell and thermocouple. Then, p-nitrobenzoyl chloride (23.57 gm, 0.127 mole) was added incrementally over 20 minutes; a slight exotherm (2° C.) was observed. The aromatic substrate (0.064 mole) was dissolved in a minimum volume of dichloroethane (typically, <50 ml) and added incrementally to the flask so that the temperature of the reaction did not exceed 30° C. Addition of the aromatic substrate was generally complete within 45 minutes. Subsequently, the mixture was heated under reflux for 3.5 hours at which time the reaction was deemed complete. On cooling, quenching (in 500 ml of 7% hydrochloric acid-ice water) and filtering the reaction product a crude bis-[4-nitrobenzoyl]arene was obtained. The resulting solid was washed with deionized water (3×200 ml), dried (110° C./1 mm/24 hr), and recrystallized from an appropriate solvent (e.g., dimethylacetamide or N-methyl-pyrrolidone), washing with a lower alcohol (e.g., methanol or ethanol) and then final dried (110° C./1 mm/24 hr) provide a purified bis-[nitrobenzoyl]ketone. Table 1 sets forth the aromatic substrates used in the above process and analysis regarding selectivity to the para position and product yield. All products possessed IR and NMR spectra and elemental analyses consistent with the assigned structures.

TABLE 1

PREPARATION OF BIS(4-NITROBENZOYL)ARENES

| Example | Aromatic Substrate | Mono-acylation Selectivity[a] (% para)[b] | Product (% Yield)[c] |
|---|---|---|---|
| 1 | Diphenyl ether | >99.8 | 81 |
| 2 | Biphenyl | >99.8 | 54[d] |
| 3 | Naphthalene | ~1:1 alpha/beta | Mono only[e] |
| 4 | Dibenzofuran | >99.8 | 72 |
| 5 | p-Terphenyl | >98[f] | 82 |
| 6 | Fluorene | — | 32[g] |

[a]Monoacylation carried out under the conditions of Example 1 by addition of 1 equivalent of p-nitrobenzoyl chloride to a mixture of 1 equivalent of the aromatic substrate and 1.5 equivalents of aluminum trichloride at 30° C.
[b]Evaluated by capillary column GLC and NMR.
[c]Isolated, recrystallized yield.
[d]Product consisted of a 1:2.7 mixture of mono:diacylation products, as measured by NMR.
[e]No diacylation observed by NMR.
[f]Sensitivity limited by compound insolubility.
[g]Yield diminished by samples taken to monitor reaction and to determine recrystallization solvent.

EXAMPLES 7-12

Preparation of bis(aminophenoxyketo)arenes by nucleophilic displacement

In this series of examples, bis-[nitrophenyl ketones] were converted to the bis(aminophenoxyketo)arenes by reacting the desired bis-[4-nitrobenzoyl]arene with the desired aminophenol. More specifically dimethylacetamide (110 ml), anhydrous toluene (110 ml), anhydrous potassium carbonate (20.73 gm, 0.150 mole), the desired bis-[4-nitrobenzoyl]arene (0.0595 mole) selected from Examples 1-6 and the desired aminophenol (0.01190 mole) were combined in a 500 ml three-neck round bottom flask. The flask was equipped with a magnetic stir bar, condenser and Dean-Stark trap, static nitrogen line, and thermowell and thermocouple. The resulting mixture was heated to reflux and solvent was removed until the pot temperature rose to 140° C. After heating under reflux for 17 hours, the mixture was cooled to room temperature, poured into ice water (500 ml) and filtered. Crystallization of the residue from n-butanol provided the pure bis(aminophenoxyketo)arene. All products possessed IR and NMR spectra and elemental analyses consistent with the assigned structures. Table 2 sets forth specific arene substrates used in forming the bis-[nitrophenylketone] and the specific aminophenols used in the reaction as well as product yield, for compounds prepared by this process.

TABLE 2
PREPARATION OF BIS(AMINOPHENOXYKETO)ARENES

| Example | Aromatic Substrate | Aminophenol | Product (1); Yield (%)[a] |
|---|---|---|---|
| 7 | Diphenyl ether | 3-aminophenol | 74 |
| 8 | Diphenyl ether | 2-(4-aminophenyl)-2-(4-hydroxyphenyl)propane | 87 |
| 9 | Dibenzofuran | 3-aminophenol | 22[b] |
| 10 | Dibenzofuran | 2-(4-aminophenyl)-2-(4-hydroxyphenyl)propane | 70 |
| 11 | p-Terphenyl | 3-aminophenol | 66 |
| 12 | p-Terphenyl | 4-aminophenol | 42 |

[a] Isolated, recrystallized yield
[b] Yield diminished by samples taken to monitor reaction and to determine recrystallization solvent

EXAMPLE 3

Preparation of Polyimide from bis(aminophenoxyketo)arene

In this process a one liter polymerization vessel was charged with 10 g (0.0126 mol) of the ether-ketone diamine prepared in Example 8 and 32 g of dimethylacetamide which was freshly distilled from barium oxide. A solution of the components was obtained by gently warming the mixture to a ca. 40° C. With mechanical stirring, 5.36 g (0.01206 mol) of 5,5'-[2,2,2-trifluoro-1-(trifluoromethyl)ethylidene]bis-1,3-isobenzofuranedione (6F-dianhydride) was added proportionately over 25 min so that the solution temperature would not exceed 40° C. An additional 29 g of dimethylacetamide was then added and the solution was stirred at room temperature for 17 hours. Imidazation of the polyamic acid solution was performed by adding 9.81 g (0.0961 mol) of acetic anhydride and 2.43 g (0.0240 mol) of triethylamine to the polymer solution and heating to 65° C. for 3 hours with stirring. Addition of 26 g of dimethylacetamide then cooling the solution resulted in a polyimide solution of 15% solids content. This product solution was stable at room temperature for at least 60 days; no cloudiness or precipitation was observed.

Films of the polyimide (ca. 100 microns thick) were obtained by casting the product solution on a glass plate then vacuum drying at ca. 70° C./10 mm Hg for 17 hrs. Residual solvent present in the films was determined to be less than 1 wt %. The resulting polyimide had a Tg of 225° C. as determined by differential scanning calorimeter (DSC). Physical properties of the polyimide film are summarized in Table 3.

TABLE 3

| Tensile Modulus | 255,000 psi |
|---|---|
| Yield Strength | 14,800 psi |
| Tensile Strength at Break | 13,100 psi |
| Elongation at Break | 36% |

As shown by the data in Table 3, the polyimide films had high tensile strength with moderate tensile molecules and good elongation at break. These results are indicative of a strong, but flexible polymer.

A key additional advantage of this polyimide is its solubility in dimethylacetamide. In contrast to many polyimides which are sparingly soluble (<5 wt %), this polyimide can be stored and used as a concentrated solution.

What is claimed is:

1. A bis-(aminophenylketone) compound represented by the structures:

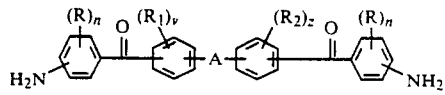

wherein R, $R_1$ and $R_2$ are hydrogen, or $C_{1-4}$ alkyl, n, v and z independently of one another are 0 to 2 if $R_1$ or $R_2$ are alkyl and wherein A is a single bond or represents

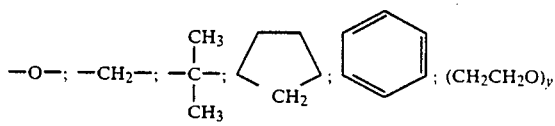

where y is 2 to 10; and

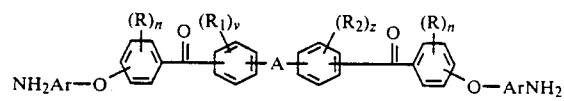

wherein R, $R_1$ and $R_2$ are hydrogen, or $C_{1-4}$ alkyl, n, v and z independently of one another are 0 to 2 if $R_1$ or $R_2$ are alkyl and wherein A is a single bond or represents

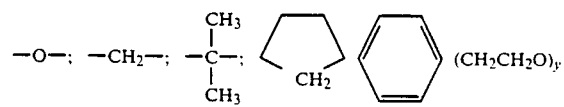

where y is 2 to 10; and Ar is naphthalene or phenylene.

2. The compound of claim 1 represented by Formula I wherein R is hydrogen.

3. The compound of claim 2 wherein $R_1$ and $R_2$ are hydrogen.

4. The compound of claim 3 wherein A is —O—.

5. The compound of claim 3 wherein A is $(CH_2CH_2O)_y$ where y is 2 to 10.

6. The compound of claim 3 wherein A is

7. The compound of claim 3 wherein A is meta-phenylene.

8. The compound of claim 3 wherein A is para-phenylene.

9. The compound of claim 1 represented by Formula II wherein R is hydrogen.

10. The compound of claim 9 wherein $R_1$ and $R_2$ are hydrogen.

11. The compound of claim 9 wherein A is —O—.

12. The compound of claim 10 wherein A is $(CH_2CH_2O)_y$ where y is 2 to 10.

13. The compound of claim 10 wherein A is

14. The compound of claim 10 wherein Ar is phenylene and A is —O—.

* * * * *